United States Patent [19]

Wagner

[11] 4,063,074
[45] Dec. 13, 1977

[54] DEVICE FOR MEASURING RADIATION ABSORPTION OR RADIATION EMISSION DISTRIBUTIONS IN A PLANE THROUGH A BODY

[75] Inventor: Wolfgang Wagner, Norderstedt, Germany

[73] Assignee: U.S. Philips Corporation, New York, N.Y.

[21] Appl. No.: 610,445

[22] Filed: Sept. 4, 1975

[30] Foreign Application Priority Data

Sept. 5, 1974 Germany ............................. 2442412

[51] Int. Cl.$^2$ ....................... G01T 1/16; G01N 23/02; G06F 15/52

[52] U.S. Cl. ................................ 364/414; 250/445 T; 250/369; 364/300; 364/527

[58] Field of Search ........... 235/151.3, 151.35, 151.31; 444/1; 250/445 T, 445 R, 341, 252, 362, 369

[56]  References Cited

U.S. PATENT DOCUMENTS

| | | | |
|---|---|---|---|
| 3,486,025 | 12/1969 | Brinkerhoff et al. ............... | 250/83.3 |
| 3,703,726 | 11/1972 | Stephenson ............................. | 444/1 |
| 3,751,643 | 8/1973 | Dill et al. ...................... | 235/151.3 X |
| 3,783,251 | 1/1974 | Pavkovich ............................ | 444/1 X |
| 3,784,820 | 1/1974 | Miraldi ............................... | 250/362 |
| 3,818,201 | 6/1974 | Hartwich et al. .............. | 235/151.31 |
| 3,852,603 | 12/1974 | Muehllehner ........................ | 250/369 |
| 3,905,045 | 9/1975 | Nickel ....................................... | 444/1 |
| 3,924,131 | 12/1975 | Hounsfield ................... | 250/445 T X |
| 3,936,636 | 2/1976 | Percival ........................... | 250/369 X |
| 3,947,684 | 3/1976 | Ikebe et al. .......................... | 250/369 |

Primary Examiner—Edward J. Wise
Attorney, Agent, or Firm—Frank R. Trifari

[57]  ABSTRACT

For measuring the absorption from measuring values whereby the radiation attenuation in a plane of a body is measured, a large number of calculations must be performed. When use is made of a digital computer, a large quantity of storage locations and a long calculating time are required. According to the invention, use is made of a charge storage tube wherein the correction values calculated in a preprocessing unit on the basis of the measuring values are superimposed, so that a substantial reduction of the calculation time and a reduction of the number of storage locations are realized.

8 Claims, 6 Drawing Figures

DEVICE FOR MEASURING RADIATION ABSORPTION OR RADIATION EMISSION DISTRIBUTIONS IN A PLANE THROUGH A BODY

The invention relates to a device for measuring the distribution of the absorption or of the emission of radiation in a plane of a body, the absorption or the emission of the body being measured in a large number of measuring series in a large number of directions situated in the plane, each measuring series comprising a number of absorption measuring values or emission measuring values measured along mutually at least approximately parallel straight lines, the absorption or the emission in discrete points of the plane being calculated on the basis of the measuring values and displayed.

A device of this kind is known (German Offenlegungsschrift 1,941,433). The absorption in a (human) body is measured therein by means of a radiator which, in conjunction with a radiation detector measuring the radiation behind the body, is displaced perpendicular to the direction of the radiation, the detector measuring a series of measuring values (measuring series) which is a measure for the absorption of the radiation along the straight line through the body determined by the position of the radiator and the detector. Following such a measuring series, the radiator detector system is rotated and a subsequent measuring series is performed at another angle with respect to the body, etc. In another embodiment of the described apparatus, use is made of a radiator and a number of detectors which are arranged behind the body to be examined on a circular arc around the radiator, the straight lines through the body, along which the absorption is measured, slightly diverging and extending only approximately parallel to each other.

From the measuring values obtained, the absorption in the discrete points or regions covered by the measurement cannot be simply reconstructed, because the measuring values do not represent a measure for the absorption in discrete points, but rather for the absorption along a line described during the measurement through the body to be examined. Mathematically this means that from the line integrals of a function (absorption, emission, density, etc.) along a large number of intersecting straight lines the value of this function in discrete points of the plane defined by the straight lines must be calculated.

This problem also occurs in the measurement of the distribution of the radioactivity in biological objects marked by radioactivity, and also in the calculation of macromolecular layers (viruses and the like) measured by means of an electron microscope, and also in the examination of layers of technical objects (for example, materials examination) by means of penetrating radiation, such as X-rays.

In known devices of the kind set forth, the calculation of the function (absorption, emission or the like) in the discrete points is calculated from the line integrals of this function (= measuring value), using one of the arithmetic processes known for these purposes, by means of a digital computer, which controls a suitable display apparatus after completion of the calculation.

The duration of the calculation time and the extent of the required digital storage capacity are drawbacks of this known device. The long calculation time is due to the fact that during the completion of the program a large number of interpolations (between $10^7$ and $10^9$) and hence a large number of multiplications, are required, which give rise to long calculation times; moreover the sequential completion of the program steps and the steps required for the internal computer control also prolong the calculation time. The large storage capacity is required for the storage of intermediate results. As a result, the installation is more expensive. Finally, the long calculation time on the one hand and the need for a large storage capacity on the other hand restrict the number of points in the plane for which absorption, emission and the like can be calculated. In practice these values are calculated for approximately 10,000 (100 × 100) points. As a result, the spatial resolution is limited, and the interpretation of the image is hampered by the grid-like display.

The invention has for its object to provide a device of the kind set forth wherein a short calculation time and a small storage capacity are realized by way of a simple construction.

To this end, a device of the kind set forth is characterized in that it comprises:

a. a preprocessing unit which calculates for each measuring value of a measuring series a correction value from the other measuring values of this measuring series in accordance with a predetermined function, b. a cathode-ray tube device which comprises at least one cathode-ray tube, whereby the charges are superimposed on adjacent strips on a target which is suitable for storage, the position and the direction of the said strips corresponding to the position and the direction of the straight lines during the measurement of each time a measuring value, the value of the charge built-up on a strip being determined by the correction value calculated for this measuring value, c. a control section which controls the preprocessing unit and the cathode-ray tube device such that the cathode-ray tube device stores the correction value each time calculated while the preprocessing unit calculates the next correction value.

The invention is based on a calculation process which is already known for these objects (see, for example, Proc. Nat. Acad. Sci. USA, Vol. 68, No. 9, pages 2236–2249, dated September 1971) wherein for each measuring value M a correction value K is calculated which results from a convolution of the measuring values of a measuring series. Each measuring value of the measuring series is multiplied by a weighting factor, and the correction value for a measuring value is determined from the sum of the products thus formed. For different known methods different weighting factors are used; however, the weighting factors are generally proportioned such that the measuring values in the vicinity of the measuring value whose correction value is to be calculated have a greater effect on the correction value than measuring values of more distant measuring locations. The absorption (emission or the like) in a point of the plane is calculated by means of these correction values in that the correction values associated with the measuring values, which are thus influenced by the absorption (emission and the like) in the relevant measuring point are added (i.e., the correction values are added which are associated with measuring values measured along straight lines through the body which intersect each other in the relevant point).

According to the invention, the calculation is divided into sub-operations, in a first operation and calculation of correction values K from the measuring values M being effected by a preprocessing unit, while the described adding of the correction values is effected on a target of cathode-ray tube device.

The invention will be described in detail hereinafter with reference to the drawing.

Figure 1:
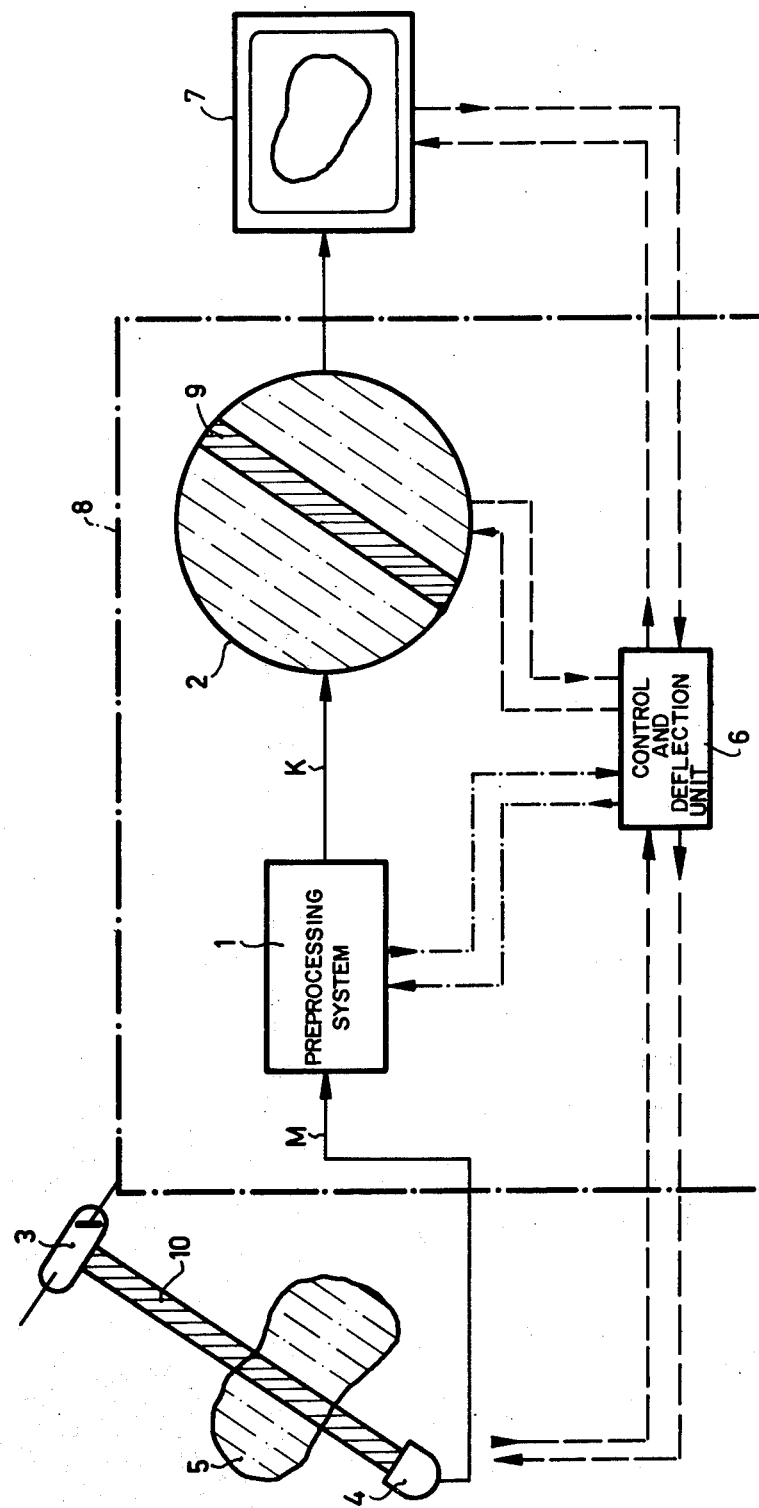
FIG. 1 shows a block diagram of a device according to the invention.

FIG. 1 diagrammatically shows a preprocessing system 1 and a target 2 of a cathode-ray tube device which is not further shown. The input of the preprocessing unit receives the measuring values. These values are supplied by a measuring device comprising a radiator 3 and a detector 4 for measuring the absorption of a body 5. These measuring values are usually proportional to the logarithm of the ratio of the intensity of the ratio in front of and behind the body. The preprocessing unit 1 calculates the correction value for each measuring value from further measuring values obtained by measurements at the same angle for a given measuring series by adding the measuring values weights in the described manner. A correction value K thus obtained controls, for example, the intensity of the electron beam of a cathode-ray tube, the said beam being guided at a constant speed and causing a charge distribution on the target. A control and deflection unit 6 controls the deflection of the electron beam such that a charge strip 9 formed on the target by the electron beam has the same position and direction with respect to an arbitrary reference system as the radiator-detector system 3, 4 during the measurement of the measuring value M associated with the correction value K. In the drawing this is indicated in that the (shaded) charge strip 9 is shown on the target at an angle equal to the angle at which the beam 10 emitted by the radiator 3 intersects the body 5. Correction values associated with measuring values measured by parallel displacement of the radiator/detector system 3, 4 are shown to be parallel displaced on the target 2. The measuring values of another measuring series, recorded at a different measuring angle however, are shown on the target as strips having a corresponding angular rotation. When all correction values have been superimposed on the target in accordance with the position and the direction of the associated measuring values during the measurement, the target has a charge distribution which corresponds to the distribution of the density or the absorption in the discrete points of the plane covered by the measurement. Subsequently, the charge distribution on the target 2 can be read and applied to an image display apparatus 7 or to an image store. The measuring system 3, 4 and the image display apparatus 7 can be of a known type, so they need not be elaborated herein. The part of the device which is relevant to the present invention is enclosed by a stroke-dot line 8.

As appears from the foregoing, the actual calculation of the spatial distribution of the absorption or the emission density is performed on the basis of the measuring values M by the preprocessing system 1 and by means of the target of the cathode-ray tube device 2. The control and deflection device 6 has no calculation function, but only coordinates the calculation of the correction values K and the superimposition of the charge strips on the target modulated in accordance with these correction values. Therefore, the control section 6 may have a comparatively simple construction. This section controls the preprocessing unit and the cathode-ray tube such that the on the target of the cathode-ray tube a charge strip is produced whose charge density is proportional to the correction value, the position and the direction thereof being determined by the position and the direction of the measuring system during the calculation of the associated measuring value, while the preprocessing system already calculates the next correction value. Moreover, this section coordinates the completion of measurement and calculation such that the preprocessing system processes the measuring values of a measuring series, while the measuring system 3, 4 calculates the measuring values of the next measuring series. The correction value calculated by the preprocessing system is subsequently applied directly as a charge strip on the target of the cathode-ray tube, so that after the calculation of the correction value for the last measuring value of the last measuring series only this correction value still has to be provided on the target, after which the charge distribution on the target corresponds to the pursued distribution function. The units which are important to the invention will be described in detail hereinafter.

a. The preprocessing unit

Figure 2:
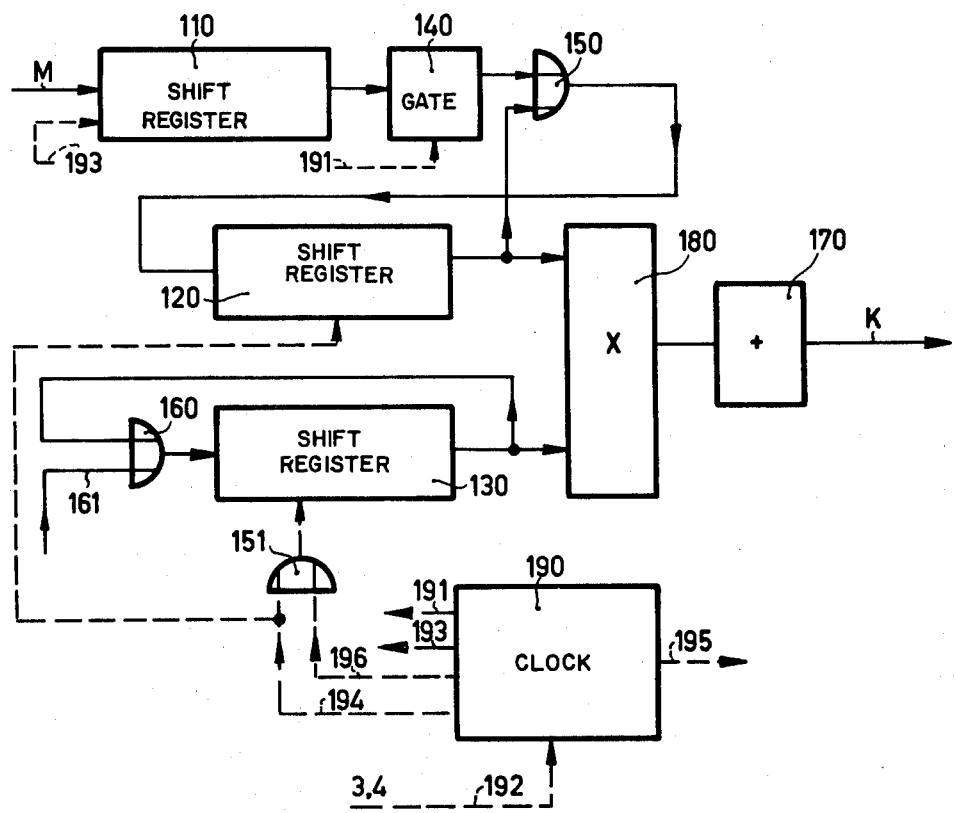
FIG. 2 shows a block diagram of the preprocessing unit therein.

FIG. 2 shows the block diagram of the preprocessing unit, uninterrupted lines indicating, like in FIG. 1, connections which are required for signal processing, the broken lines indicating connections required for the control of the individual components. The preprocessing system comprises three shift registers 110, 120 and 130, each of which comprises twice as many register cells as there are measuring values in a single measuring series. The registers are constructed such that the contents thereof can be shifted from the left to the right under the influence of a digital control signal. The shift registers 110 and 120 each time take up the measuring values, while the shift register 130 stores the weighting factors.

A gate 140 opens or blocks the connection between the shift register 110 and the shift register 120 in dependence of a signal on a control line 191 which is generated by an internal clock 190. OR-gates 150 and 160 enable cyclical shifting of the contents of the shift registers 120 and 130 as well as the taking over of an external signal. A multiplication unit 180 multiplies the signals each time present on the output of the shift registers 120 and 130, i.e. each time a measuring value having a weighting factor, and applies the result to an accumulating adder 170 which adds this product to the already calculated value. The clock 190 ensures that the calculation in the preprocessing system can be asynchronous with respect to the processes in the other systems, it being necessary to exchange commands between the preprocessing system and the control section 6 (FIG. 1) only at the beginning (or the end) of a calculation cycle.

The completion in time of a calculation in the preprocessing system will be described hereinafter. First of all, it is assumed that the contents of the shift registers 110 and 120 are zero (the reset lines required for this purpose are not shown in FIG. 2), and that the weighting factors are stored in the correct sequence in the shift register 130. When the measuring values of a measuring series have been obtained, the clock receives a signal from the measuring system 2, 4 via the line 192, the clock then supplying a signal, via the control line 193, which ensures that the measuring values M are taken up in the shift register 110 in the sequence in which they have been measured. Subsequently, the gate 140 is opened via the control line 191, with the result that the measuring values can be transferred from the shift register 110 to the shift register 120. Subsequently, the gate 140 is closed again. The first calculation cycle then starts. Via the control line 194, the measuring values and weighting factors stored in the shift registers 120 and 130, respectively, are cyclically shifted together. In reaction to each clock signal, the multiplication circuit 180 performs a multiplication of the values each time appearing on the outputs of the shift registers 120 and 130, the adding unit 170 then adding the product to the already calculated product. At the end of N clock signals (N = number of register cells of a shift register), the final calculated correction value K is present on the output of the accumulating adder 170. The completion of this first calculation cycle is signalled to the control section 6 via the line 195, a strip having a charge density proportional to the correction value K then being written on the target. At this instant the measuring values and weighting factors are in the same positions as at the beginning of the calculation cycles, this is due to the cyclical shifting of the contents of the shift registers 120 and 130 over N register locations.

Before the beginning of each subsequent calculation cycle, during which the correction value each time added to another measuring value is to be calculated, a gate 151 changes, via the control line 196, the position of the weighting factors in the shift register 130 relative to the position of the measuring values in the shift register 120. Subsequently, the calculation cycle is completed in the same manner as the first calculation cycle. This is repeated until the associated correction value has been calculated for each measuring value of a measuring series. The preprocessing of a measuring series has then been completed. Because the gate 140 is closed during the completion of the calculation cycles, the measuring values of the next measuring series can already be input in the register 110, independent of the calculation operations in the shift registers 120 and 130, so that after the completion of the calculation of all correction values of a measuring series, the register 120 can be loaded again and the calculation of the correction values of the new measuring series can be started without delay.

The individual parts of the preprocessing unit can be of analog or digital construction. However, it is advisable to use an analog accumulating adder 170 if also an analog multiplier is used. Moreover, the shift register 130 would have to be designed as a digital component, because the weighting factors must be saved for a very long period of time, unless the user introduces other weighting factors (via the line 161). Digital-to-analog convertors or analog-to-digital convertors must then possibly be present for converting the analog signal into a digital signal or vice versa.

The shift registers 110, 120 can be constructed as analog shift registers (for example, charge-coupled devices, bucket stores or bucket brigade circuits) or as digital shift registers, each measuring value being stored as an information word in a register cell which consists of a series of parallel arranged binary storage cells. The multiplication circuit 180 can be a digital multiplier with fixed wiring; however, an analog multiplier circuit or a multiplying digital-to-analog convertor which operates accurately and very fast is a less expensive solution. The adding circuit 170 may also be of a digital design. However, it can alternatively comprise an analog integrator which is followed by a sample-and-hold amplifier, which, after each calculation cycle, briefly stores the calculated correction value prior to the writing on the target of the cathode-ray tube. The construction of the gate circuit 140 and the OR-circuits 150, 151 and 160 is adapted to the construction of the registers 110, 120 and 130.

b. The cathode-ray tube device for the superimposition of the correction values.

As has already been stated, the cathode-ray tube device serves to superimpose the correction values each time calculated for a strip, in order to measure the pursued function values (absorption, emission or the like) in the plane examined. The measuring values always have the same sign, but the correction values derived from the measuring values generally can have a negative or a positive sign. This means that on the target positive and negative charges would have to be superimposed; this is not readily possible.

FIGS. 3a to 3d show embodiments or cathode-ray tube devices which allow the superimposition of correction values of different sign. All four embodiments have in common that they use one or two cathode-ray tubes comprising a target which can store positive or negative electrical charges in arbitrary locations, and that they use a deflection section which, under the control of the control section 6, generates deflection voltages or deflection currents which direct the electron beam on the target along a strip whose position and direction correspond to the position and direction of the measuring system during the measurement of the measuring value associated with the correction value to be recorded. The deflection direction of the electron beam is changed by a change of the ratio of the sawtooth currents for the X-direction and the Y-direction; a parallel shift of the deflection direction of the electron beam is effected in that an additive component is superimposed on the deflection currents, or in that the deflection currents are delayed in time with respect to each other. The width of the electron beam is adjusted such that its half-value width corresponds approximately to the strip width.

Figure 3A:
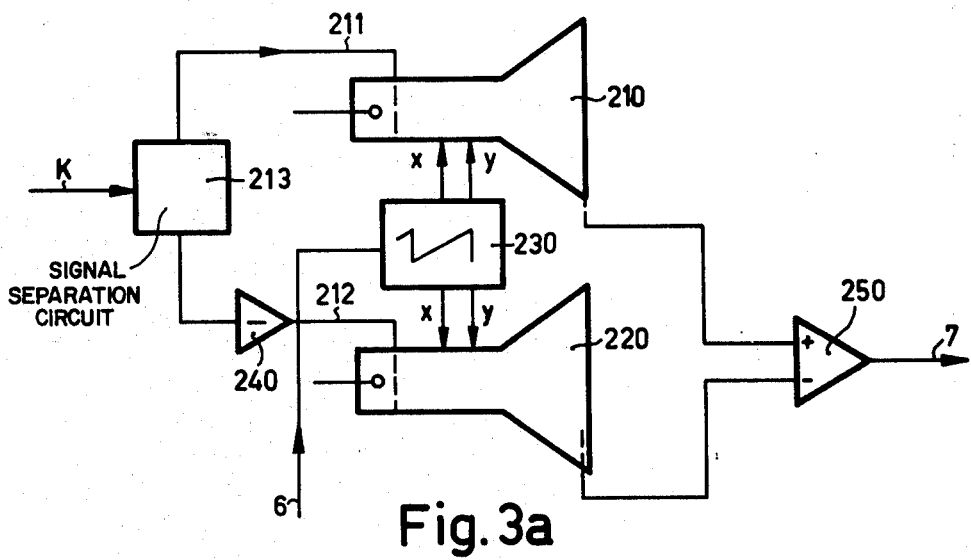
FIGS. 3a to 3d show different methods of realizing the cathode-ray tube device for superimposing the correction values.

FIG. 3a shows an embodiment comprising two identical storage tubes 210 and 220. A storage tube corresponds to a cathode-ray tube incorporating magnetic deflection and a dielectric target. An electron beam incident on the target releases secondary electrons which are removed by a grid arranged in front of the target. If the voltage difference between cathode and target is sufficient (> 100 V), the emission factor of the secondary electrons $\delta > 1$ and the target location whereon the electron beam is incident is positively charged. Because the target surface is not conductive, this charge is maintained, i.e. the target has a storing function, the charge stored being inter alia proportional to the product I.T, I being the intensity of the electron beam and T the radiation time. Using the deflection generator controlled by the control section 6, the electron beam of both tubes is passed over the target at a uniform speed such that the strip described on the target by the electron beam occupies the same position with respect to the strip of the other correction values as the measuring system during the measurement of the associated measuring value with respect to the position thereof during the measurement of the other measuring values.

The intensity of the electron beam is determined by the bias voltage on the grids of the cathode-ray tubes 210 and 220 which is applied via the lines 211 and 212, respectively. These bias voltages are derived from the correction values K, a signal separation circuit 213 ensuring that the line 211 receives only positive correction values, while the negative correction values are applied to the line 212 via an inverting circuit 240 which reverses the polarity of the signal. The tube 210 superimposes the positive correction values, and the tube 220 superimposes the negative correction values. For generating a superimposition image of all correction values, the charge images on the targets of the two tubes 210 and 220 are synchronously scanned (for example, by a T.V.-standard) and applied, via a differential amplifier, to the image display apparatus 7, to an image store or the like, where the pursued distribution is displayed or stored, respectively.

Figure 3B:
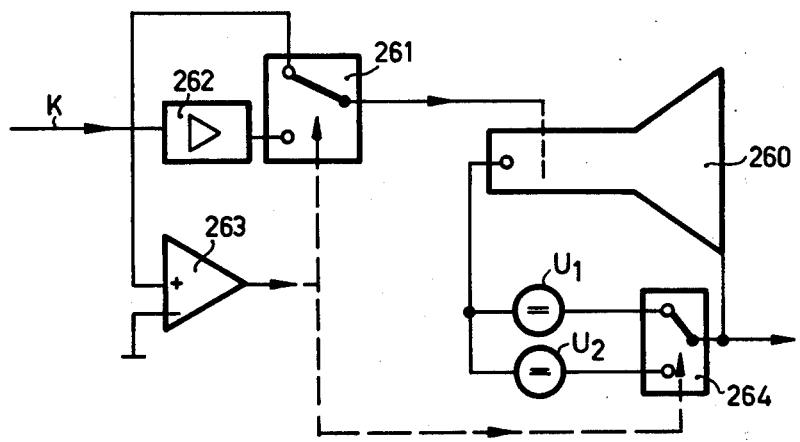

FIG. 3b shows an embodiment wherein a single storage tube is sufficient. The deflection and the focussing of the electron beam are effected in the same manner as described with reference to FIG. 3a. In this embodiment use is made of the fact that the emission factor of the secondary electrons is smaller than 1, if the voltage between cathode and target is comparatively small ($U_2$). In this case the location on the target on which the electron beam impinges is negatively charged, i.e. a small amount is subtracted from a positive charge already present on the target.

The correction value is then applied to the grid of the storage tube 260 via a switch 261. In the upper position of the switch, the correction value is directly present on the grid of the storage tube, while in the lower position the correction value is applied to the grid of the storage tube via an inverting amplifier 262. A sign discriminator 263 controls the switch 261 such that in the case of a positive correction value, the switch is in the upper position, while the switch is in the lower position in the case of a negative correction value. A voltage is thus applied to the grid of the storage tube which is proportional to the amount of the correction value. The sign discriminator 263, moreover, controls a switch 264 which switches the voltage between cathode and target from a high value ($U_1$) to a low value ($U_2$), so that in the one case a positive charge is superimposed on the target, and in the other case a negative charge. In any case it must be taken into account that the negative charging current at the low voltage $U_2$ between cathode and anode is smaller than the positive charging current at the voltage $U_1$. Therefore, the amplification factor of the inverting amplifier 262 is proportioned such that the amount of the charge variation on the target is exclusively determined by the amount of the correction value.

In this embodiment, like in the embodiment shown in FIG. 3a, types of storage tube for the interference-free reading of the charge distribution as well as types where the charge distribution is reduced during reading can be used. In the latter case the charge distribution built-up must be intermediately stored in an external image store.

Figure 3C:
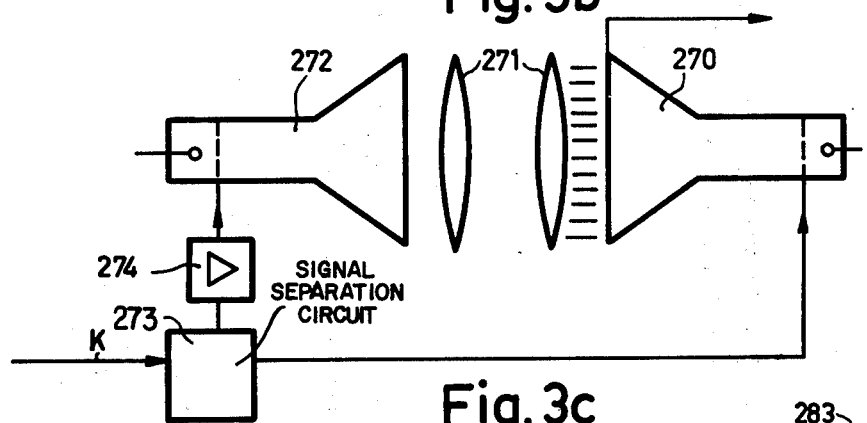

The embodiment shown in FIG. 3c utilizes the fact that a vidicon camera tube, notably constructed as a tube of the type Plumbicon, can store a positive charge distribution on the photocathode for a few seconds. A camera tube 270 is then directed, via an optical transmission path 271, onto the display screen of a video display tube 272. The correction value is applied to a signal separation circuit 273, which applies positive correction values to the grid of the camera tube 270 and negative values to the grid of the video display tube 272, via an inverting amplifier 274. The photocathode of the camera tube 270 is uniformly illuminated before the start of transmission, so that a uniform positive charge is built up.

If the scanning beam of the camera tube is modulated with the positive correction values, the charge is partly reduced along the strips described by the electron beam on the photocathode of the camera tube. The electron beam thus produces a charge distribution which is complementary to the correction values. The electron beam of the video display tube is modulated with the negative correction values, the electron beam thereof being deflected in synchronism with the electron beam of the camera tube. The strips written on the video display tube cause an increase of the positive charge on the photocathode of the camera tube which is proportional to the negative correction values written on the display tube 272. In this way an addition or subtraction of the charge distribution on the photocathode of the camera tube 270 is obtained, the gain of the inverting amplifier then having to be proportioned such that the built-up or reduced charge quantity is independent of the sign of the correction value. The output signal of the camera tube is again applied to an image store.

Figure 3D:
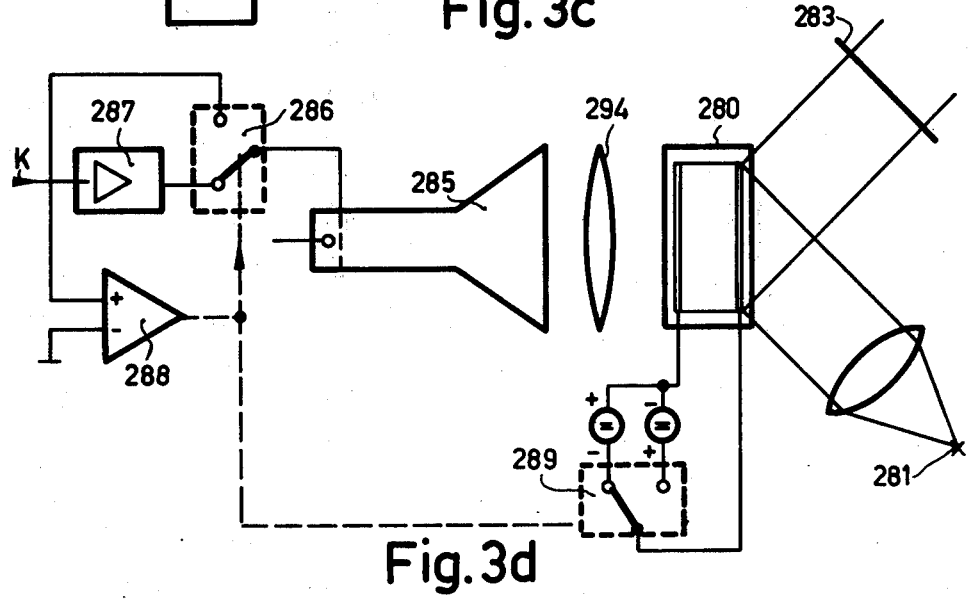

Finally FIG. 3d shows an embodiment of the cathode-ray tube device wherein a so-termed titus tube is used. A tube of this kind offers the possibility of storing an optical image applied to the input thereof. A charge distribution is built up on a dielectric mirror included in the titus tube in accordance with the brightness of the optical image. The polarity of the stored charges is dependent of the polarity of the direct voltage applied between the two outer transparent electrodes. For reading the stored charge images, the output side of the titus tube is irradiated by a source 281 of linearly polarized light. The light is reflected by the dielectric mirror, the light being rotated in the polarization direction by a crystal, dependent of the sign and of the value of the charge stored on the dielectric mirror. The rotation of the polarization direction is made visible by means of an analyser 283.

The input side of the titus tube 280 is directed onto the display screen of a video display tube 285 via an optic system 284. The intensity of the electron beam of the video display tube is modulated by the amount of the correction value. To this end, the correction value K can be applied to the modulation grid of the video display tube 285 via a switch 286 in a direct manner on the one side, and on the other side via an inverting amplifier 287. As has already been described with reference to FIG. 3b, the switch 286 is controlled by a sign recognition circuit 288 such that the electron flow is proportional to the amount of the correction value each time applied. As a result, the brightness of the strips recorded on the display screen is also proportional to the amount of the correction values. Because the sign recognition circuit 288 switches over, via a further switch 289, the polarity of the direct voltage between the two outer electrodes of the titus tube in dependence of the polarity of the correction value, it is achieved that the charge strip generated on the display screen of the video display tube in accordance with the brightness strip has a polarity which corresponds to the polarity of the correction value. The device shown in FIG. 3d offers the advantage that the calculated two-dimensional distribution of the absorption etc. can be optically read, so that the titus tube not only serves as a storage element, but at the same time as an optical image display apparatus.

c. The control section

The control and deflection device has the following functions:

a. co-ordinating the calculation processes of preprocessing section and cathode-ray tube device, and supplying the deflection section of the cathode-ray tube device with the parameters required for registering the strip in the correct position;

b. the additional co-ordination of the device according to the invention with the exterior, for example, with the system formed by radiator 3 and detector 4 on the one side, and the image display, image storage, and image printing units on the other side.

c. serving as junction especially between the preprocessing system and the operating personel, the operating personnel introducing, for example, new weighting factors or the number of measuring series required for the calculation via this point. To this end, a small digital process computer or a microprocess computing circuit must be added.

What is claimed is:

1. A device for measuring the spatial distribution of the absorption or emission of radiation in a plane of a body, comprising:
   means for measuring the absorption or emission of the body in a large number of directions all situated in the plane, the measurements forming a multiplicity of measuring series, each measuring series comprising a multiplicity of measuring values measured along approximately parallel straight lines, the lines of different series being oriented in different directions;
   a preprocessing unit for calculating a correction value corresponding to each measuring value from the measuring values of the same series in accordance with a predetermined function,
   a cathode-ray tube device having a charge storage target area for superposing correction values, the target area being scanned in parallel strips corresponding in position and direction with the straight lines of the measuring values, the amount of charge added or taken away from each strip being determined by the correction value of the corresponding measuring value; and
   a control section for controlling the preprocessing unit and the cathode-ray tube device such that while the cathode-ray tube scans a strip corresponding to a measuring value, the preprocessing unit calculates the correction value corresponding to the next measuring value.

2. A device as defined in claim 1 wherein the preprocessing unit comprises:
   a first shift register for receiving and storing successive measuring values as they are measured;
   a second shift register coupled to the first shift register for receiving and storing an entire measuring series from the first shift register;
   a third shift register for storing weighting factors;
   a multiplication unit coupled to the second and third shift registers for multiplying the measuring values of a stored measuring series by corresponding weighting factors; and
   an accumulating adding member coupled to the multiplication unit for adding the products calculated by the multiplication unit.

3. A device as defined in claim 2 wherein the second and third shift registers are shifted relative to each other for calculating correction values corresponding to different measuring values of the stored measuring series.

4. A device as claimed in claim 1, wherein the correction values are superimposed by means of two electronic storage tubes, the deflection systems of which are controlled in synchronism with each other, the electron beam of the one storage tube being modulated with the positive correction values and the electron beam of the other storage tube being modulated with the negative correction values, the negative correction values being applied to the control grid of the storage tube via an inverter stage, the charge distribution on the targets of the two storage tubes being read in synchronism with each other and being applied, via a differential amplifier, to an image display unit, or an image store.

5. A device as claimed in claim 1, wherein the cathode-ray tube device comprises a single electronic storage tube, the electron beam intensity of which is controlled by the amount of the correction value, the voltage between cathode and target being switched from a high value to a low value in accordance with the sign of the correction value.

6. A device as claimed in claim 1, wherein the cathode-ray tube device comprises a vidicon tube which is focussed on the display screen of a vidicon display tube the deflection of the two cathode-ray tubes being synchronously controlled, and, after uniform illumination of the vidicon tube, the scanning beam thereof being controlled by the positive correction values, the electron beam of the video display tube, however, being controlled by the negative correction values via an inverter stage.

7. A device as claimed in claim 1, wherein the electron beam of a video display tube directed in accordance with the position and the direction during the measurement of the measuring value, is modulated each time with the amount of the correction value, a titus tube being optically coupled to the display screen of the video display tube, the polarity of the direct voltage applied to the outer electrodes of the titus tube being switched over in accordance with the sign of the applied correction values.

8. A device as claimed in claim 1, wherein the electron beam of the cathode ray tube device is focussed such that the half-width value thereof corresponds approximately to the width of one strip.

* * * * *